US012797374B2

(12) United States Patent
Kim et al.

(10) Patent No.: US 12,797,374 B2
(45) Date of Patent: Nov. 17, 2026

(54) COMPOSITION FOR TREATING CORONAVIRUS DISEASE-19, COMPRISING PHENANTHROINDOLIZIDINE AND PHENANTHROQUINOLIZIDINE ALKALOID DERIVATIVES, OPTICAL ISOMER THEREOF, OR PHARMACEUTICALLY ACCEPTABLE SALTS THEREOF AS ACTIVE INGREDIENT

(71) Applicant: SEOUL NATIONAL UNIVERSITY R & DB FOUNDATION, Seoul (KR)

(72) Inventors: Sanghee Kim, Seoul (KR); Sang Kook Lee, Seoul (KR); Jayoung Song, Seoul (KR); Yongseok Kwon, Seoul (KR); Mee Hyein Kim, Daejeon (KR); Jin Soo Shin, Daejeon (KR); Ye Jin Jang, Daejeon (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 810 days.

(21) Appl. No.: 18/042,801

(22) PCT Filed: Apr. 30, 2021

(86) PCT No.: PCT/KR2021/005513

§ 371 (c)(1),
(2) Date: Feb. 24, 2023

(87) PCT Pub. No.: WO2022/045520

PCT Pub. Date: Mar. 3, 2022

(65) Prior Publication Data

US 2023/0233538 A1 Jul. 27, 2023

(30) Foreign Application Priority Data

Aug. 26, 2020 (KR) ........................ 10-2020-0108099

(51) Int. Cl.
*A61K 31/437* (2006.01)
*A61K 31/4375* (2006.01)

(52) U.S. Cl.
CPC ........ *A61K 31/437* (2013.01); *A61K 31/4375* (2013.01)

(58) Field of Classification Search
CPC .................................................... A61K 31/437
See application file for complete search history.

(56) References Cited

U.S. PATENT DOCUMENTS 8,440,649 B2 5/2013 Lee et al.

FOREIGN PATENT DOCUMENTS

KR 10-2017-0088695 A 8/2017
KR 20170088695 A * 8/2017 ........... C07D 471/04

OTHER PUBLICATIONS

Kwon et al., "Design, Synthesis, and Biological Activity of Sulfonamide Analogues of Antofine and Cryptopleurine as Potent and Orally Active Antitumor Agents", J. Med. Chem., 2015 (Year: 2015).*

Yang et al., "Identification of phenanthroindolizines and phenanthroquinolizidines as novel potent anti-coronaviral agents for porcine enteropathogenic coronavirus transmissible gastroenteritis virus and human severe acute respiratory syndrome coronavirus", Elsevier, 2010 (Year: 2010).*

Allegra et al., "Immunopathology of SARS-CoV-2 Infection: Immune Cells and Mediators, Prognostic Factors, and Immune-Therapeutic Implications", International Journal of Molecular Sciences, vol. 21, No. 13, Jul. 6, 2020 (Jul. 6, 2020), p. 4782 (19 pages).

Bhuiyan et al., "Plants Metabolites: Possibility of Natural Therapeutics Against the COVID-19 Pandemic", Frontiers in Medicine, vol. 7, article 444, 26 pages, Aug. 7, 2020 (Aug. 7, 2020).

Islam et al., "Natural products and their derivatives against coronavirus: A review of the non-clinical and pre-clinical data", Physiotherapy Research, vol. 34, No. 10, Apr. 4, 2020 (Apr. 4, 2020), pp. 2471-2492.

Lee et al., "Synthesis and Biological Evaluation of Tylophorine Derived Dibenzoquinolines as Orally Active Agents: Exploration of the Role of Tylophorine E Ring on Biological Activity", Journal of Medicinal Chemistry, vol. 55, No. 23, Dec. 4, 2012 (Dec. 4, 2012), pp. 10363-10377.

Yang et al., "Targeting Coronaviral Replication and Cellular JAK2 Mediated Dominant NF-[kappa]B Activation for Comprehensive and Ultimate Inhibition of Coronaviral Activity", Scientific Reports, vol. 7, No. 1, 13 pages, Jun. 22, 2017 (Jun. 22, 2017).

The extended European Search Report for corresponding EP 21861822. 1, 15 pages, issued Jun. 20, 2024.

Altay et al., "Current Status of COVID-19 Therapies and Drug Repositioning Applications", iScience, 2020, vol. 23, No. 101303, 12 pages.

Kubo et al., "Antimalarial Phenanthroindolizine Alkaloids from Ficus septica", Chem. Pharm. Bull., 2016, vol. 64, No. 7, pp. 957-960.

Kwon et al., "Design, Synthesis, and Biological Activity of Sulfonamide Analogues of Antofine and Cryptopleurine as Potent and Orally Active Antitumor Agents", J. Med. Chem., 2015, vol. 58, pp. 7749-7762.

Wang et al., "Synthesis and Antiviral Activities of Phenanthroindolizidine Alkaloids and Their Derivatives", J. Agric. Food Chem, 2010, vol. 58, pp. 2703-2709.

(Continued)

*Primary Examiner* — Andrew D Kosar
*Assistant Examiner* — Gillian A Hutter
(74) *Attorney, Agent, or Firm* — Vorys, Sater, Seymour and Pease LLP; Mih Suhn Koh

(57) ABSTRACT

Provided is a composition for treating coronavirus disease-19 (Corona19, COVID-19), including a phenanthroindolizidine and phenanthroquinolizidine alkaloid derivative compound, an optical isomer thereof, or a pharmaceutically acceptable salt thereof as an active ingredient. According to the presently claimed subject matter, the phenanthroindolizidine and phenanthroquinolizidine alkaloid derivative compound has excellent antiviral activity against COVID-19, and therefore can be effectively used as a composition for treating SARS coronavirus infection including COVID-19.

4 Claims, 2 Drawing Sheets

(56) References Cited

OTHER PUBLICATIONS

Yang et al., "Identification of phenanthroindolizines and phenanthroindolizidines as novel potent anti-coronaviral agents for porcine enteropathogenic coronavirus transmissible gastroenteritis virus and human severe acute respiratory syndrome coronavirus", Antiviral Research, 2010, vol. 88, pp. 160-168.

* cited by examiner

COMPOSITION FOR TREATING CORONAVIRUS DISEASE-19, COMPRISING PHENANTHROINDOLIZIDINE AND PHENANTHROQUINOLIZIDINE ALKALOID DERIVATIVES, OPTICAL ISOMER THEREOF, OR PHARMACEUTICALLY ACCEPTABLE SALTS THEREOF AS ACTIVE INGREDIENT

CROSS-REFERENCE TO RELATED APPLICATIONS

This application is a 371 of PCT/KR2021/005513 filed on Apr. 30, 2021, which claims the benefit of priority from Korean Patent Application No. 10-2020-0108099 filed on Aug. 26, 2020, the contents of each of which are incorporated herein by reference in its entirety.

TECHNICAL FIELD

The present disclosure relates to a composition for treating coronavirus disease-19 comprising phenanthroindolizidine and phenanthroquinolizidine alkaloid derivatives, an optical isomer thereof, or a pharmaceutically acceptable salt thereof as an active ingredient, etc.

BACKGROUND ART

Coronavirus is a virus belonging to the Coronaviridae family, and is generally found in various mammals including humans as well as birds. There are many different types of coronaviruses and the coronavirus is known to cause both respiratory and digestive infections depending on the characteristics and host of the virus. Human coronavirus (HCoV) accounts for 15-35% of respiratory viral infections depending on the season. Most coronavirus infections cause mild symptoms like a cold, but some develop into pneumonia, bronchitis, etc. However, within a few months from the time when the infection first began in China in the winter of 2002, SARS-CoV, a novel infectious disease virus that has spread worldwide to Hong Kong, Singapore, Canada, etc.; MERS coronavirus (MERS-CoV), which has been reported in 26 countries including the Middle East, Europe, Africa, Asia, the United States, etc. since it was first reported in Saudi Arabia in 2012; and cases where fatal respiratory diseases (e.g., coronavirus disease-19 (SARS-CoV-2)) are rapidly spreading to each of Asian countries including Thailand, Japan, and Korea, North America, and various European countries after the outbreak in Wuhan, China in December 2019 are induced, have also been reported.

The pathogen of coronavirus disease-19 (Corona 19, COVID-19) is "SARS-CoV-2" and it is an RNA virus belonging to the family Coronaviridae. The main symptoms of COVID-19 infection are fever and respiratory symptoms (cough, sore throat, dyspnea), and symptoms such as headache, muscle pain, hemoptysis, nausea, chills, chest pain, and diarrhea may appear depending on the patient. Since there is no vaccine or treatment for the infection, only symptomatic treatment is possible depending on the patient's symptoms. The incubation period is estimated to be 2-14 days, similar to other coronaviruses. While healthy adults are more likely to recover over time, the infection can be fatal for people with low immunity, such as the elderly or people with underlying medical conditions. In some cases, the infection may progress to acute respiratory distress syndrome (ARDS), acute lung injury, septic shock, and acute kidney injury, and in severe cases, death. The global fatality rate varies greatly by country and age, but is reported to be about 3.4% (based on WHO 3.5). COVID-19 is transmitted when droplets (saliva) of an infected person penetrate the respiratory tract or the mucous membranes of the eyes, nose, and mouth.

Currently, the U.S. Food and Drug Administration (FDA) has approved the emergency use of Remdesivir as a therapeutic agent for a severe patient with COVID-19, which is a drug developed by Gilead Sciences in the U.S. as a therapeutic agent for Ebola trials, but this is not an official treatment but rather a treatment for severe patients with low blood oxygen levels or those who need to be treated with oxygen therapy, an artificial respirator, etc. In addition, Remdesivir has not yet been clinically confirmed with regard to its side effects, and although Remdesivir has the effect of reducing the recovery period of patients by 4 days, it also has limitations as a therapeutic agent for COVID-19 in that there is no significant difference in patient mortality, etc. Therefore, there is an urgent need to develop an effective therapeutic agent for the treatment of COVID-19.

Representative materials of phenanthroindolizidine and phenanthroquinolizidine alkaloids include antofine, tylophorine, tylocrebine, and cryptopleurine. These compounds described above have been isolated from plants, and methods for preparing the same through an organic synthesis process have also been reported.

As prior art documents related to phenanthroindolizidine and phenanthroquinolizidine alkaloid derivative compounds, Korean Patent Application Publication No. 10-2011-0079661 and Korean Patent Application Publication No. 10-2011-0081199 disclose phenanthroindolizidine derivatives and NF-κB inhibitors including the same as an active ingredient, and the likelihood of using the same as an anticancer agent for antopine and cryptopleurin analogs has been disclosed in Korean Patent Application Publication No. 10-2017-0088695.

However, the applicability of the phenanthroindolizidine and phenanthroquinolizidine alkaloid derivative compounds as a therapeutic agent for COVID-19 has not been disclosed.

DISCLOSURE

Technical Problem

The present disclosure has been devised to solve the needs in prior art as described above, and the present inventors have confirmed that phenanthroindolizidine and phenanthroquinolizidine alkaloid derivatives have excellent inhibitory effects on coronavirus activity, thereby confirming their effects on preventing and treating coronavirus infection disease, as a result, completing the present disclosure based on the same.

As such, an object of the present disclosure is to provide a pharmaceutical composition for preventing or treating coronavirus disease-19 comprising phenanthroindolizidine and phenanthroquinolizidine alkaloid derivative compounds represented by Formula 1 below, an optical isomer thereof, or a pharmaceutically acceptable salt thereof as an active ingredient:

[Formula 1]

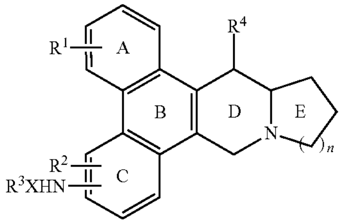

wherein in Formula 1 above, $R^1$ and $R^2$ are each independently one or more hydrogen, halogen, hydroxy, $C_1$-$C_5$ alkyl, $C_1$-$C_5$ alkoxy, carboxylic acid, amino, or $C_1$-$C_5$ alkyl amino;

$R^3$ is $C_1$-$C_5$ alkyl, $C_1$-$C_5$ alkoxy, or aryl; $R^4$ is hydrogen or hydroxy;

X is CO or $SO_2$; and n is an integer of 1 or 2.

However, the technical problem to be solved by the present disclosure is not limited to the above-mentioned problems, and other problems to be solved not mentioned will be clearly understood by those skilled in the art from the description hereinbelow.

Technical Solution

In order to achieve the object of the present disclosure as described above, the present disclosure provides a pharmaceutical composition for preventing or treating coronavirus disease-19 comprising phenanthroindolizidine and phenanthroquinolizidine alkaloid derivative compounds represented by Formula 1, an optical isomer thereof, or a pharmaceutically acceptable salt thereof as an active ingredient:

[Formula 1]

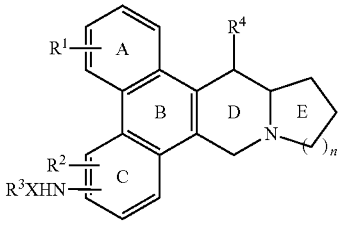

wherein in Formula 1 above, $R^1$ and $R^2$ are each independently one or more hydrogen, halogen, hydroxy, $C_1$-$C_5$ alkyl, $C_1$-$C_5$ alkoxy, carboxylic acid, amino, or $C_1$-$C_5$ alkyl amino;

$R^3$ is $C_1$-$C_5$ alkyl, $C_1$-$C_5$ alkoxy, or aryl; $R^4$ is hydrogen or hydroxy;

X is CO or $SO_2$; and n is an integer of 1 or 2.

In an exemplary embodiment of the present disclosure, the phenanthroindolizidine and phenanthroquinolizidine alkaloid derivative compounds may be one or more selected from the group consisting of the following compounds, but is not limited thereto:

(R)—N-(2,3-dimethoxy-9,11,12,13,13a,14-hexahydrodibenzo-[f,h]pyrrolo[1,2-b]isoquinolin-6-yl)methanesulfonamide;

(R)—N-(2,3-dimethoxy-11,12,13,14,14a,15-hexahydro-9H-dibenzo[f,h]pirido[1,2-b]isoquinolin-6-yl)methanesulfonamide;

methyl(2,3-dimethoxy-11,12,13,14,14a,15-hexahydro-9H-dibenzo[f,h]pirido[1,2-b]isoquinolin-6-yl)carbamate;

N-(2,3-dimethoxy-11,12,13,14,14a,15-hexahydro-9H-dibenzo[f,h]pirido[1,2-b]isoquinolin-6-yl)propan-2-sulfonamide;

N-(2,3-dimethoxy-11,12,13,14,14a,15-hexahydro-9H-dibenzo[f,h]pirido[1,2-b]isoquinolin-6-yl)benzenesulfonamide;

N-(15-hydroxy-2,3-dimethoxy-11,12,13,14,14a,15-hexahydro-9H-dibenzo[f,h]pirido[1,2-b]isoquinolin-6-yl) methanesulfonamide;

N-(3-chloro-2-methoxy-11,12,13,14,14a,15-hexahydro-9H-dibenzo[f,h]pirido[1,2-b]isoquinolin-6-yl)methanesulfonamide;

N-(3-hydroxy-2-methoxy-11,12,13,14,14a,15-hexahydro-9H-dibenzo[f,h]pirido[1,2-b]isoquinolin-6-yl)methanesulfonamide;

N-(3-ethyl-2-methoxy-11,12,13,14,14a,15-hexahydro-9H-dibenzo[f,h]pirido[1,2-b]isoquinolin-6-yl)methanesulfonamide;

2-methoxy-6-(methylsulfonamido)-11,12,13,14,14a,15-hexahydro-9H-dibenzo[f,h]pirido[1,2-b]isoquinolin-3-carboxylic acid;

N-(3-amino-2-methoxy-11,12,13,14,14a,15-hexahydro-9H-dibenzo[f,h]pirido[1,2-b]isoquinolin-6-yl)methanesulfonamide;

N-(2-methoxy-3-(methylamino)-11,12,13,14,14a,15-hexahydro-9H-dibenzo[f,h]pirido[1,2-b]isoquinolin-6-yl) methanesulfonamide;

N-(2,3,7-trimethoxy-11,12,13,14,14a,15-hexahydro-9H-dibenzo[f,h]pirido[1,2-b]isoquinolin-6-yl)methanesulfonamide;

N-(6-ethyl-2,3-dimethoxy-11,12,13,14,14a,15-hexahydro-9H-dibenzo[f,h]pirido[1,2-b]isoquinolin-5-yl)methanesulfonamide;

N-(7-chloro-2,3-dimethoxy-11,12,13,14,14a,15-hexahydro-9H-dibenzo[f,h]pirido[1,2-b]isoquinolin-6-yl)methanesulfonamide; and N-(2,3-dimethoxy-11,12,13,14,14a,15-hexahydro-9H-dibenzo[f,h]pirido[1,2-b]isoquinolin-6-yl)acetamide.

In another exemplary embodiment of the present disclosure, the phenanthroindolizidine and phenanthroquinolizidine alkaloid derivative compounds may be one or more selected from the group consisting of the following compounds, but is not limited thereto:

(R)—N-(2,3-dimethoxy-9,11,12,13,13a,14-hexahydrodibenzo-[f,h]pyrrolo[1,2-b]isoquinolin-6-yl)methanesulfonamide;

(R)—N-(2,3-dimethoxy-11,12,13,14,14a,15-hexahydro-9H-dibenzo[f,h]pirido[1,2-b]isoquinolin-6-yl)methanesulfonamide; and methyl(2,3-dimethoxy-11,12,13,14,14a,15-hexahydro-9H-dibenzo[f,h]pirido[1,2-b]isoquinolin-6-yl)carbamate.

In still another exemplary embodiment of the present disclosure, the coronavirus may be severe acute respiratory syndrome coronavirus 2 (SARS-CoV-2), but is not limited thereto.

Additionally, the present disclosure provides a method for preventing or treating coronavirus disease-19, comprising administering the composition comprising phenanthroindolizidine and phenanthroquinolizidine alkaloid derivative compounds represented by Formula 1, an optical isomer thereof, or a pharmaceutically acceptable salt thereof as an active ingredient to a subject.

Additionally, the present disclosure provides a use of a composition comprising the phenanthroindolizidine and phenanthroquinolizidine alkaloid derivative compounds represented by Formula 1, an optical isomer thereof, or a pharmaceutically acceptable salt thereof as an active ingredient for preventing or treating coronavirus disease-19.

Additionally, the present disclosure provides a use of the phenanthroindolizidine and phenanthroquinolizidine alkaloid derivative compounds represented by Formula 1, an optical isomer thereof, or a pharmaceutically acceptable salt thereof for preparation of an agent for treating coronavirus disease-19.

Advantageous Effects

The phenanthroindolizidine and phenanthroquinolizidine alkaloid derivative compounds of the present disclosure have excellent inhibitory effect on the activity of SARS-CoV-2 virus, which is a causative pathogen of coronavirus disease-19 (COVID-19), and therefore, can be effectively used as a pharmaceutical composition for treating coronavirus disease-19.

BEST MODES

Figure 1:
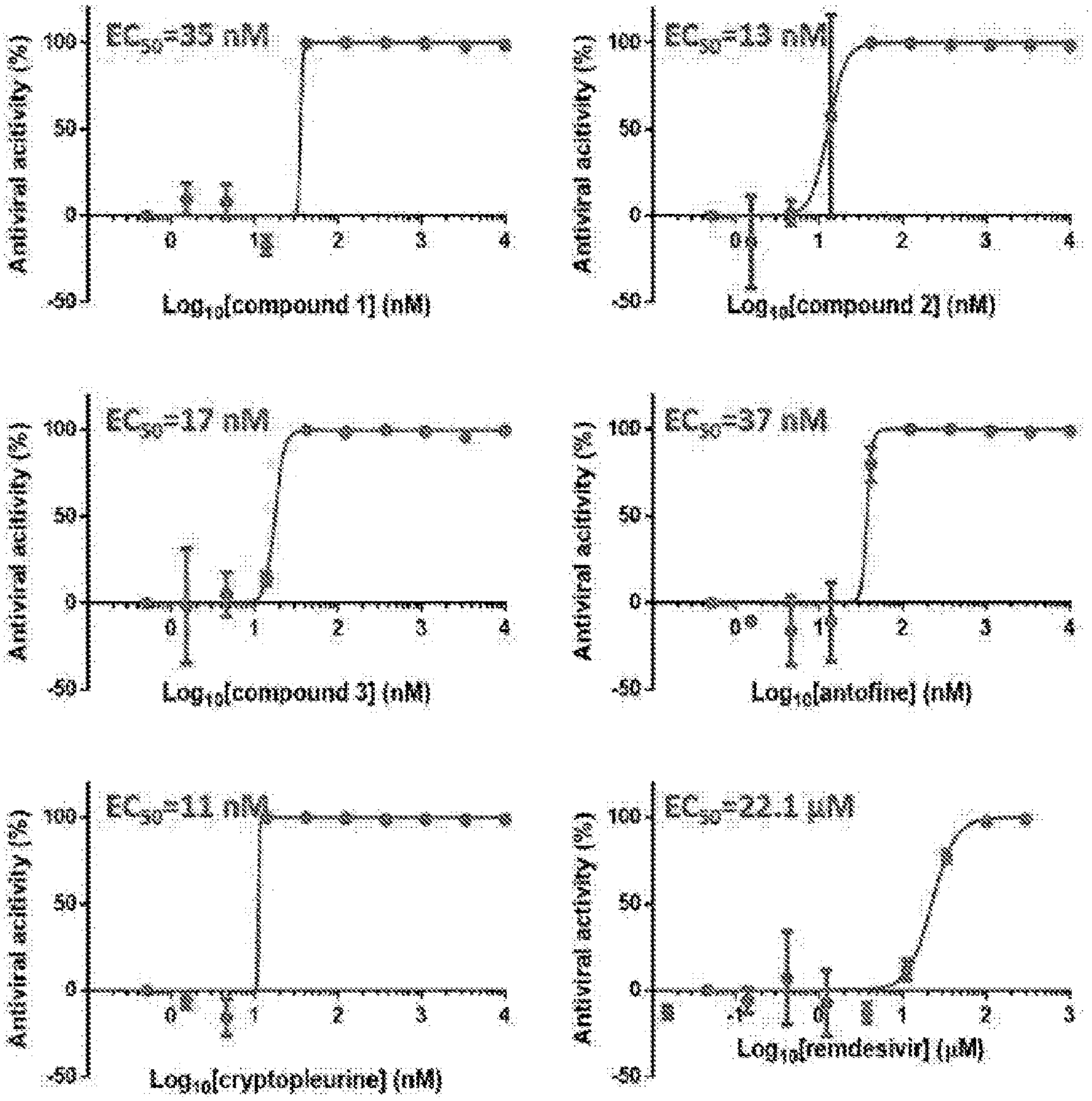
FIG. 1 shows the inhibitory effect of phenanthroindolizidine and phenanthroquinolizidine alkaloid derivative compounds on the activity of SARS-CoV-2 virus.

The present inventors have confirmed that the phenanthroindolizidine and phenanthroquinolizidine alkaloid derivative compounds represented by Formula 1 have excellent inhibitory effects on the activity of coronavirus while having low cytotoxicity, thereby completing the present disclosure (see Examples of the present disclosure).

Accordingly, the present disclosure relates to a composition for preventing, improving, or treating coronavirus disease-19 comprising phenanthroindolizidine and phenanthroquinolizidine alkaloid derivative compounds represented by Formula 1 below, an optical isomer thereof, or a pharmaceutically acceptable salt thereof as an active ingredient.

[Formula 1]

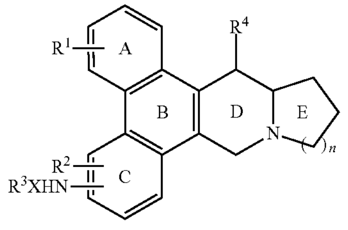

In Formula 1 above, $R^1$ and $R^2$ are each independently one or more hydrogen, halogen, hydroxy, $C_1$-$C_5$ alkyl, $C_1$-$C_5$ alkoxy, carboxylic acid, amino, or $C_1$-$C_5$ alkyl amino;

$R^3$ is $C_1$-$C_5$ alkyl, $C_1$-$C_5$ alkoxy, or aryl; $R^4$ is hydrogen or hydroxy;

X is CO or $SO_2$; and n is an integer of 1 or 2.

The compound of Formula 1 may be specifically exemplified as follows:

(R)—N-(2,3-dimethoxy-9,11,12,13,13a,14-hexahydrodibenzo-[f,h]pyrrolo[1,2-b]isoquinolin-6-yl)methanesulfonamide (Compound 1);

(R)—N-(2,3-dimethoxy-11,12,13,14,14a,15-hexahydro-9H-dibenzo[f,h]pirido[1,2-b]isoquinolin-6-yl)methanesulfonamide (Compound 2);

methyl(2,3-dimethoxy-11,12,13,14,14a,15-hexahydro-9H-dibenzo[f,h]pirido[1,2-b]isoquinolin-6-yl)carbamate (Compound 3);

N-(2,3-dimethoxy-11,12,13,14,14a,15-hexahydro-9H-dibenzo[f,h]pirido[1,2-b]isoquinolin-6-yl)propan-2-sulfonamide (Compound 4);

N-(2,3-dimethoxy-11,12,13,14,14a,15-hexahydro-9H-dibenzo[f,h]pirido[1,2-b]isoquinolin-6-yl)benzenesulfonamide (Compound 5);

N-(15-hydroxy-2,3-dimethoxy-11,12,13,14,14a,15-hexahydro-9H-dibenzo[f,h]pirido[1,2-b]isoquinolin-6-yl) methanesulfonamide (Compound 6);

N-(3-chloro-2-methoxy-11,12,13,14,14a,15-hexahydro-9H-dibenzo[f,h]pirido[1,2-b]isoquinolin-6-yl)methanesulfonamide (Compound 7);

N-(3-hydroxy-2-methoxy-11,12,13,14,14a,15-hexahydro-9H-dibenzo[f,h]pirido[1,2-b]isoquinolin-6-yl)methanesulfonamide (Compound 8);

N-(3-ethyl-2-methoxy-11,12,13,14,14a,15-hexahydro-9H-dibenzo[f,h]pirido[1,2-b]isoquinolin-6-yl)methanesulfonamide (Compound 9);

2-methoxy-6-(methylsulfonamido)-11,12,13,14,14a,15-hexahydro-9H-dibenzo[f,h]pirido[1,2-b]isoquinolin-3-carboxylic acid (Compound 10);

N-(3-amino-2-methoxy-11,12,13,14,14a,15-hexahydro-9H-dibenzo[f,h]pirido[1,2-b]isoquinolin-6-yl)methanesulfonamide (Compound 11);

N-(2-methoxy-3-(methylamino)-11,12,13,14,14a,15-hexahydro-9H-dibenzo[f,h]pirido[1,2-b]isoquinolin-6-yl) methanesulfonamide (Compound 12);

N-(2,3,7-trimethoxy-11,12,13,14,14a,15-hexahydro-9H-dibenzo[f,h]pirido[1,2-b]isoquinolin-6-yl)methanesulfonamide (Compound 13);

N-(6-ethyl-2,3-dimethoxy-11,12,13,14,14a,15-hexahydro-9H-dibenzo[f,h]pirido[1,2-b]isoquinolin-5-yl)methanesulfonamide (Compound 14);

N-(7-chloro-2,3-dimethoxy-11,12,13,14,14a,15-hexahydro-9H-dibenzo[f,h]pirido[1,2-b]isoquinolin-6-yl)methanesulfonamide (Compound 15); or N-(2,3-dimethoxy-11,12,13,14,14a,15-hexahydro-9H-dibenzo[f,h]pirido[1,2-b]isoquinolin-6-yl)acetamide (Compound 16), but is not limited thereto.

Hereinafter, the present disclosure will be described in detail.

As used herein, the term "$C_{1-5}$ alkyl" refers to a monovalent alkyl group having 1 to 5 carbon atoms. The term comprises functional groups such as methyl, ethyl, n-propyl, i-propyl, n-butyl, i-butyl, tert-butyl, 1-methylpropyl, etc.

Alkyl, and other substituents including an alkyl moiety described herein comprise both linear and branched chain forms.

As used herein, the term "$C_{1-5}$ alkoxy" refers to an —O—R group, in which R represents "$C_1$-$C_5$ alkyl". Preferred alkoxy groups comprise, for example, methoxy, ethoxy, propoxy, n-butoxy, tert-butoxy, 1-methylpropoxy, etc.

As used herein, the term "aryl" refers to a functional group, in which the hydrogen of an aromatic hydrocarbon is removed in a molecule, for example, phenyl, tolyl, xylene, biphenolyl, naphthyl, anthryl, phenanthryl, etc.

As used herein, the term "$C_{1-5}$ alkyl amino" comprises all of the substituents in which a $C_{1-5}$ alkyl group and an amino group (—$NH_2$) are bound together.

As used herein, the term "halogen" may comprise fluoro (F), chloro (Cl), and bromo (Br), and iodine (I).

The substituents including alkyl, alkoxy, and other alkyl moieties described in the present disclosure include both linear and branched chain forms.

In Formula 1, $R_1$ may be substituted on the A ring, and $R_2$ and $R_3$ may each independently be substituted on the C ring.

The compound according to the present disclosure may be isolated from nature or prepared by chemical synthesis of compounds known in the art.

As used herein, the term "coronavirus" is a virus species included in the order Nidoviridae, the family Coronaviridae, the subfamily Coronavirinae or Torovirinae. It was first discovered in chickens in 1937, followed by animals such as dogs, pigs, and birds, and was also discovered in humans in 1965. It is known that the causative agent of Severe Acute Respiratory Syndrome (SARS), which first appeared in mid-March 2003 and caused more than 100 deaths and infected 3,000 patients worldwide, is a novel (mutant) coronavirus. It is mainly divided into three serotypes (the 1st, 2nd, and 3rd serotypes), and in particular, the 2nd serotype originated from bats and was found to be transmitted to humans, and thus the infection caused by heterogeneous transmission has become a problem.

In the present disclosure, the coronavirus may be, for example, human coronavirus 229E (HCoV-229E), human coronavirus OC43 (HCoV—OC43), severe acute respiratory syndrome coronavirus (SARS-CoV), human coronavirus NL63 (HCoV-NL63, New Haven coronavirus), human coronavirus HKU1, middle east respiratory syndrome Coronavirus (MERS-CoV), severe acute respiratory syndrome coronavirus 2 (SARS-Cov-2 or 2019 novel coronavirus or 2019-nCoV); and preferably, severe acute respiratory syndrome coronavirus 2 (SARS-CoV-2), but the coronavirus is not limited thereto.

In the present disclosure, the coronavirus infectious disease may be a coronavirus respiratory infection disease. The viral respiratory infection diseases may show symptoms such as cough, sneezing, headache, stuffy nose, sore throat, diarrhea, discoloration of fingers or toes, conjunctivitis, high fever, wheezing, bronchitis, bronchiolitis, pneumonia, asthma, loss of smell and taste, and respiratory failure.

In the present disclosure, the coronavirus infectious disease may be, more specifically, coronavirus disease-19 (COVID-19), but is not limited thereto.

The present disclosure may also include the pharmaceutically acceptable salt as an active ingredient. As used herein, the term "pharmaceutically acceptable salt" includes salts derived from pharmaceutically acceptable inorganic acids, organic acids, or bases.

Examples of suitable acids include hydrochloric acid, hydrobromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, gluconic acid, naphthalene-2-sulfonic acid, benzenesulfonic acid, etc. Acid addition salts may be prepared by conventional methods, for example, by dissolving a compound in an excess amount of an aqueous acid solution, and precipitating the salt using a water-miscible organic solvent such as methanol, ethanol, acetone, or acetonitrile. Additionally, acid addition salts may be prepared by heating an equimolar amount of the compound and an acid or alcohol in water and then drying the mixture by evaporation, or by suction filtration of the precipitated salt.

Salts derived from suitable bases may include, but are not limited to, alkali metals (e.g., sodium, potassium, etc.), alkaline earth metals (e.g., magnesium, etc.), ammonium, etc. The alkali metal or alkaline earth metal salt may be obtained, for example, by dissolving a compound in an excess amount of an alkali metal hydroxide or alkaline earth metal hydroxide solution, filtering the undissolved compound salt, and then evaporating and drying the filtrate. In particular, it is pharmaceutically suitable to prepare a sodium, potassium, or calcium salt as the metal salt, and the corresponding silver salt may be obtained by reacting an alkali metal or alkaline earth metal salt with a suitable silver salt (e.g., silver nitrate).

The amount of the compound in the composition of the present disclosure may be appropriately adjusted depending on the symptoms of the disease, the degree of progression of the symptoms, the conditions of the patient, etc., for example, 0.0001-99.9 wt % or 0.001-50 wt % based on the total weight of the composition, but is not limited thereto. The amount ratio is a value based on the dry amount from which the solvent is removed.

The pharmaceutical composition according to the present disclosure may further include suitable carriers, excipients, and diluents which are commonly used in the preparation of pharmaceutical compositions. The excipient may be, for example, one or more selected from the group consisting of a diluent, a binder, a disintegrant, a lubricant, an adsorbent, a humectant, a film-coating material, and a controlled-release additive.

The pharmaceutical composition according to the present invention may be used by being formulated, according to commonly used methods, into a form such as powders, granules, sustained-release-type granules, enteric granules, liquids, eye drops, elixirs, emulsions, suspensions, spirits, troches, aromatic water, lemonades, tablets, sustained-release-type tablets, enteric tablets, sublingual tablets, hard capsules, soft capsules, sustained-release-type capsules, enteric capsules, pills, tinctures, soft extracts, dry extracts, fluid extracts, injections, capsules, perfusates, or a preparation for external use, such as plasters, lotions, pastes, sprays, inhalants, patches, sterile injectable solutions, or aerosols. The preparation for external use may have a formulation such as creams, gels, patches, sprays, ointments, plasters, lotions, liniments, pastes, or cataplasmas.

As the carrier, the excipient, and the diluent that may be included in the pharmaceutical composition according to the present invention, lactose, dextrose, sucrose, oligosaccharides, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil may be used.

For formulation, commonly used diluents or excipients such as fillers, thickeners, binders, wetting agents, disintegrants, and surfactants are used.

As additives of tablets, powders, granules, capsules, pills, and troches according to the present invention, excipients such as corn starch, potato starch, wheat starch, lactose, white sugar, glucose, fructose, D-mannitol, precipitated calcium carbonate, synthetic aluminum silicate, dibasic calcium phosphate, calcium sulfate, sodium chloride, sodium hydrogen carbonate, purified lanolin, microcrystalline cellulose, dextrin, sodium alginate, methyl cellulose, sodium carboxymethylcellulose, kaolin, urea, colloidal silica gel, hydroxypropyl starch, hydroxypropyl methylcellulose (HPMC), HPMC 1928, HPMC 2208, HPMC 2906, HPMC 2910, propylene glycol, casein, calcium lactate, and Primojel; and binders such as gelatin, Arabic gum, ethanol, agar powder, cellulose acetate phthalate, carboxymethylcellulose, calcium carboxymethylcellulose, glucose, purified water, sodium caseinate, glycerin, stearic acid, sodium carboxymethylcellulose, sodium methylcellulose, methylcellulose, microcrystalline cellulose, dextrin, hydroxycellulose, hydroxypropyl starch, hydroxymethylcellulose, purified shellac, starch, hydroxypropyl cellulose, hydroxypropyl methylcellulose, polyvinyl alcohol, and polyvinylpyrrolidone may be used, and disintegrants such as hydroxypropyl methylcellulose, corn starch, agar powder, methylcellulose, bentonite, hydroxypropyl starch, sodium carboxymethylcellulose, sodium alginate, calcium carboxymethylcellulose, calcium citrate, sodium lauryl sulfate, silicic anhydride, 1-hydroxypropylcellulose, dextran, ion-exchange resin, polyvinyl acetate, formaldehyde-treated casein and gelatin, alginic acid, amylose, guar gum, sodium bicarbonate, polyvinylpyrrolidone, calcium phosphate, gelled starch, Arabic gum, amylopectin, pectin, sodium polyphosphate, ethyl cellulose, white sugar, magnesium aluminum silicate, a di-sorbitol solution, and light anhydrous silicic acid; and lubricants such as calcium stearate, magnesium stearate, stearic acid, hydrogenated vegetable oil, talc, lycopodium powder, kaolin, Vaseline, sodium stearate, cacao butter, sodium salicylate, magnesium salicylate, polyethylene glycol (PEG) 4000, PEG 6000, liquid paraffin, hydrogenated soybean oil (Lubri wax), aluminum stearate, zinc stearate, sodium lauryl sulfate, magnesium oxide, Macrogol, synthetic aluminum silicate, silicic anhydride, higher fatty acids, higher alcohols, silicone oil, paraffin oil, polyethylene glycol fatty acid ether, starch, sodium chloride, sodium acetate, sodium oleate, dl-leucine, and light anhydrous silicic acid may be used.

As additives of liquids according to the present invention, water, dilute hydrochloric acid, dilute sulfuric acid, sodium citrate, monostearic acid sucrose, polyoxyethylene sorbitol fatty acid esters (twin esters), polyoxyethylene monoalkyl ethers, lanolin ethers, lanolin esters, acetic acid, hydrochloric acid, ammonia water, ammonium carbonate, potassium hydroxide, sodium hydroxide, prolamine, polyvinylpyrrolidone, ethylcellulose, and sodium carboxymethylcellulose may be used.

In syrups according to the present invention, a white sugar solution, other sugars or sweeteners, and the like may be used, and as necessary, a fragrance, a colorant, a preservative, a stabilizer, a suspending agent, an emulsifier, a viscous agent, or the like may be used.

In emulsions according to the present invention, purified water may be used, and as necessary, an emulsifier, a preservative, a stabilizer, a fragrance, or the like may be used.

In suspensions according to the present invention, suspending agents such as acacia, tragacanth, methylcellulose, carboxymethylcellulose, sodium carboxymethylcellulose, microcrystalline cellulose, sodium alginate, hydroxypropyl methylcellulose, HPMC 1828, HPMC 2906, HPMC 2910, and the like may be used, and as necessary, a surfactant, a preservative, a stabilizer, a colorant, and a fragrance may be used.

Injections according to the present invention may include: solvents such as distilled water for injection, a 0.9% sodium chloride solution, Ringer's solution, a dextrose solution, a dextrose+sodium chloride solution, PEG, lactated Ringer's solution, ethanol, propylene glycol, non-volatile oil-sesame oil, cottonseed oil, peanut oil, soybean oil, corn oil, ethyl oleate, isopropyl myristate, and benzene benzoate; cosolvents such as sodium benzoate, sodium salicylate, sodium acetate, urea, urethane, monoethylacetamide, butazolidine, propylene glycol, the Tween series, amide nicotinate, hexamine, and dimethylacetamide; buffers such as weak acids and salts thereof (acetic acid and sodium acetate), weak bases and salts thereof (ammonia and ammonium acetate), organic compounds, proteins, albumin, peptone, and gums; isotonic agents such as sodium chloride; stabilizers such as sodium bisulfite ($NaHSO_3$) carbon dioxide gas, sodium metabisulfite ($Na_2S_2O_5$), sodium sulfite ($Na_2SO_3$), nitrogen gas ($N_2$), and ethylenediamine tetraacetic acid; sulfating agents such as 0.1% sodium bisulfide, sodium formaldehyde sulfoxylate, thiourea, disodium ethylenediaminetetraacetate, and acetone sodium bisulfite; a pain relief agent such as benzyl alcohol, chlorobutanol, procaine hydrochloride, glucose, and calcium gluconate; and suspending agents such as sodium CMC, sodium alginate, Tween 80, and aluminum monostearate.

In suppositories according to the present invention, bases such as cacao butter, lanolin, Witepsol, polyethylene glycol, glycerogelatin, methylcellulose, carboxymethylcellulose, a mixture of stearic acid and oleic acid, Subanal, cottonseed oil, peanut oil, palm oil, cacao butter+cholesterol, lecithin, lanette wax, glycerol monostearate, Tween or span, imhausen, monolan(propylene glycol monostearate), glycerin, Adeps solidus, buytyrum Tego-G, cebes Pharma 16, hexalide base 95, cotomar, Hydrokote SP, S-70-XXA, S-70-XX75 (S-70-XX95), Hydrokote 25, Hydrokote 711, idropostal, massa estrarium (A, AS, B, C, D, E, I, T), masa-MF, masupol, masupol-15, neosuppostal-N, paramount-B, supposiro OSI, OSIX, A, B, C, D, H, L, suppository base IV types AB, B, A, BC, BBG, E, BGF, C, D, 299, suppostal N, Es, Wecoby W, R, S, M, Fs, and tegester triglyceride matter (TG-95, MA, 57) may be used.

Solid preparations for oral administration include tablets, pills, powders, granules, capsules, and the like, and such solid preparations are formulated by mixing the composition with at least one excipient, e.g., starch, calcium carbonate, sucrose, lactose, gelatin, and the like. In addition to simple excipients, lubricants such as magnesium stearate and talc are also used.

Examples of liquid preparations for oral administration include suspensions, liquids for internal use, emulsions, syrups, and the like, and these liquid preparations may include, in addition to simple commonly used diluents, such as water and liquid paraffin, various types of excipients, for example, a wetting agent, a sweetener, a fragrance, a preservative, and the like. Preparations for parenteral administration include an aqueous sterile solution, a non-aqueous solvent, a suspension, an emulsion, a freeze-dried preparation, and a suppository. Non-limiting examples of the non-aqueous solvent and the suspension include propylene glycol, polyethylene glycol, a vegetable oil such as olive oil, and an injectable ester such as ethyl oleate.

The pharmaceutical composition according to the present invention is administered in a pharmaceutically effective amount. In the present invention, "the pharmaceutically effective amount" refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields.

The pharmaceutical composition according to the present disclosure may be administered as an individual therapeutic agent, may be administered in combination with other therapeutic agents, may be administered sequentially or simultaneously with conventional therapeutic agents, and may be administered once or multiple times. In consideration of all of the above factors, it is important to administer an amount capable of obtaining the maximum effect with a minimum amount without side effects, which can easily be determined by those skilled in the art to which the present disclosure pertains.

The pharmaceutical composition of the present disclosure may be administered to a subject by various routes. All modes of administration may be considered, for example, oral administration, subcutaneous injection, intraperitoneal administration, intravenous injection, intramuscular injection, paraspinal space (intrathecal) injection, sublingual administration, buccal administration, rectal insertion, vaginal insertion, ocular administration, otic administration, nasal administration, inhalation, spray through the mouth or nose, dermal administration, transdermal administration, etc.

The pharmaceutical composition of the present disclosure is determined according to the type of drug as an active ingredient along with several related factors (e.g., the disease to be treated, route of administration, patient's age, sex, weight, and severity of the disease).

As used herein, the term "subject" refers to a subject in need of treatment for a disease, and more specifically, may be a mammal of humans or non-human primates, mice, rats, dogs, cats, horses, cattle, etc., but is not limited thereto.

As used herein, the term "administration" refers to provision of a predetermined composition of the present disclosure to a subject by any suitable method.

As used herein, the term "prevention" refers to all actions that inhibit or delay the onset of a target disease; the term "treatment" refers to all actions that improve or beneficially change a target disease and metabolic abnormalities thereof by the administration of the pharmaceutical composition according to the present disclosure; and the term "improvement" refers to all actions that reduce target disease-related parameters, for example, the degree of symptoms.

Hereinafter, preferred Experimental Examples and Examples are presented to help the understanding of the present disclosure. However, the following Experimental Examples and Examples are provided only to facilitate easier understanding of the present disclosure, and the content of the present disclosure is not limited by the following Experimental Examples and Examples.

Experimental Example 1. Efficacies of Phenanthroindolizidine and Phenanthroquinolizidine Alkaloid Derivative Compounds on Inhibition of Activity of SARS-CoV-2 Virus and Analysis of Cytotoxicities Thereof In order to measure the antiviral activity of the compounds of the present disclosure against SARS-CoV-2, an image-based antiviral assay method was used.

First, one day before the test, $2\times10^4$ Vero CCL-81 cells were cultured in each well of a 96-well plate. Compounds diluted 3-fold from 10 µM to 0.5 nM were treated with Vero CCL-81 30 minutes before viral infection (MOI, 0.1). Remdesivir, which was urgently approved for the treatment of severe SARS-CoV-2 inpatients in the United States, was used as a control, and antopine and cryptopleurin were used as controls for representative natural product-derived phenanthroindolizidine and phenanthroquinolizidine alkaloids, respectively. After 48 hours of infection, the culture medium was removed and the cells were washed with phosphate buffered saline. For immunofluorescence analysis, cells were fixed with a mixture of acetone and methanol and permeabilized, and then viral spike proteins present intracellularly were fluorescently labeled using mouse anti-S antibody (GeneTex, Irvine, CA) and Alexa Fluor 488-conjugated anti-mouse goat IgG (Invitrogen, Carlsbad, CA). Fluorescence images were photographed using an Operetta high content screening system (Perkin Elmer, Waltham, MA). The number of cells expressing the spike protein in the image was calculated with Harmony software (Perkin Elmer, Waltham, MA) and used as an observation of antiviral efficacy.

The resulting cytotoxicities were measured by the degree of chromatin condensation in the cell nucleus through 4',6-henylindole (DAPI; Invitrogen) staining.

Example 1. Confirmation of Efficacy of Phenanthroindolizidine and Phenanthroquinolizidine Alkaloid Derivative Compounds on Inhibition of Activity of SARS-CoV-2 Virus The efficacy of the compound of the present disclosure on inhibition of activity of SARS-CoV-2 virus was confirmed.

As a result, as shown in FIG. 1 and Table 1, Compound 1, a phenanthroindolizidine alkaloid derivative compound, had a 50% virus proliferation inhibitory concentration with an effective concentration 50 ($EC_{50}$) of 35 nM, thus showing an effect similar to that of antofine ($EC_{50}$: 37 nM), which is a natural product-derived phenanthroindolizidine alkaloid used as a control, and Compound 1 showed about a 630-fold greater effect compared to the positive control Remdesivir ($EC_{50}$: 22 µM), which is currently used in clinical practice.

In addition, in the case of phenanthroquinolizidine alkaloid derivative Compounds 2 and 3, $EC_{50}$ was 13 nM and 17 nM, respectively, thus showing an effect similar to that of cryptopleurin ($EC_{50}$: 11 nM), which is a natural product-derived phenanthroquinolizidine alkaloid used as a control, and Compounds 2 and 3 showed about a 1,700-fold and about a 1,300-fold higher virus proliferation inhibitory ability compared to Remdesivir, respectively.

TABLE 1

| Compound | Effective Concentration 50 ($EC_{50}$) |
|---|---|
| 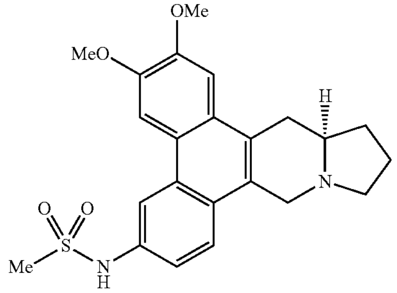 [Compound 1] | 35 nM |

TABLE 1-continued
| Compound | Effective Concentration 50 ($EC_{50}$ ) |
| --- | --- |
| 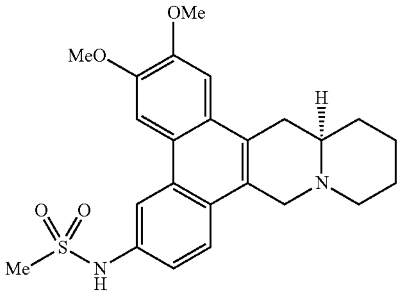 [Compound 2] | 13 nM |
| 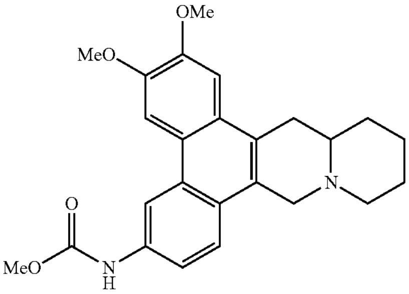 [Compound 3] | 17 nM |
| 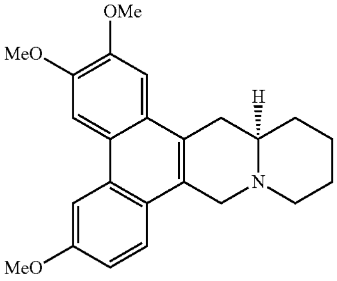 [Control group: Antofine] | 37 nM |
| 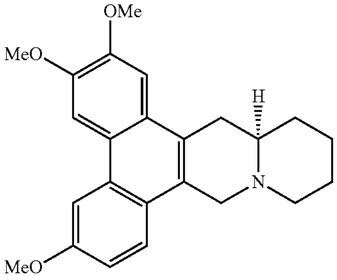 [Control group: Cryptopleurine] | 11 nM |
| [Control group: Remdesivir] | 22.1 μM |

Example 2. Confirmation of Cytotoxicity and Selectivity Index of Phenanthroindolizidine and Phenanthroquinolizidine Alkaloid Derivative Compounds The cytotoxicities of the compounds of the present disclosure and the overall virus selectivity indices resulting therefrom were confirmed.

Figure 2:
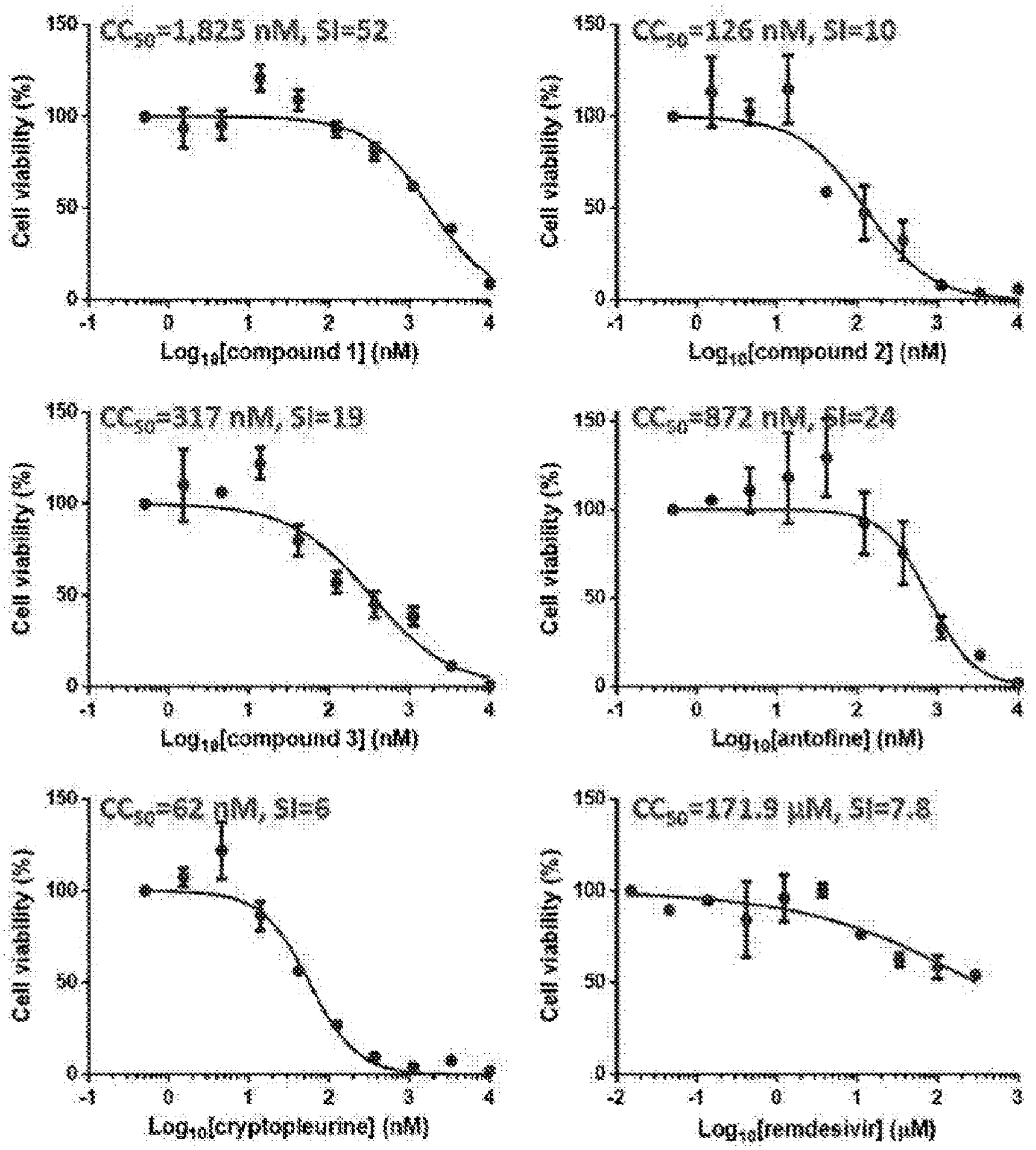
FIG. 2 shows the cytotoxicity of phenanthroindolizidine and phenanthroquinolizidine alkaloid derivative compounds against Vero CCL-81 cells.

As a result, as shown in FIG. 2 and Table 2, Compound 1 showed the weakest cytotoxicity with a cytotoxic concentration 50 ($CC_{50}$) of 1,825 nM, and the resulting selectivity index (SI) of 52, thus showing the most excellent values even compared to antofine ($CC_{50}$: 872 nM; SI 24) and Remdesivir ($CC_{50}$: 172 μM; SI 7.8) (i.e., a control group).

In addition, in the case of Compounds 2 and 3, the $CC_{50}$ was 126 nM and 317 nM, respectively, showing significantly lower cytotoxicity compared to cryptopleurin (i.e., a control group), and the selectivity index was also 10 and 19, respectively, thus showing an excellent value compared to cryptopleurin (SI 6) and Remdesivir.

As a result, the compounds of the present disclosure showed high antiviral efficacy in terms of toxicities compared to commercially available Remdesivir, and in particular, in the case of Compound 1, the activity was about 630-fold greater compared to that of Remdesivir, and the selection index was also significantly improved.

TABLE 2

| | Cytotoxic Concentration 50 | Selectivity Index |
|---|---|---|
| 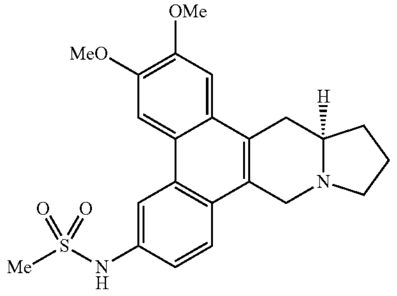 [Compound 1] | 1,825 nM | 52 |
| 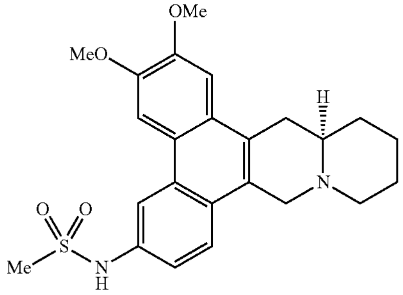 [Compound 2] | 126 nM | 10 |
| 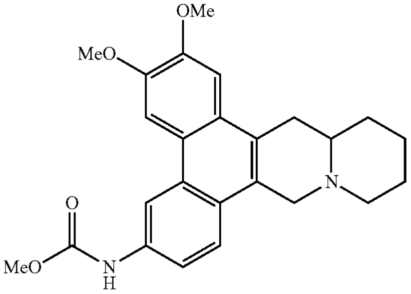 [Compound 3] | 317 nM | 19 |

TABLE 2-continued

| | Cytotoxic Concentration 50 | Selectivity Index |
|---|---|---|
| 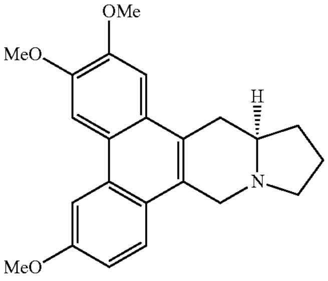 [Control group: Antofine] | 872 nM | 24 |
| 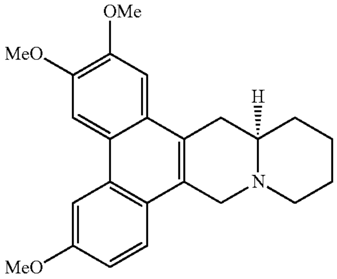 [Control group: Cryptopleurine] | 62 nM | 6 |
| [Control group: Remdesivir] | 171.9 μM | 7.8 |

In addition, Formulation Examples of the compositions comprising the compounds of the present disclosure will be described below, but the present disclosure is not intended to be limited thereto, but only to be described in detail.

Formulation Example 1. Preparation of Powder phenanthroindolizidine and phenanthroquinolizidine alkaloid derivative compounds 200 mg
lactose 100 mg
talc 10 mg The above ingredients are mixed and an airtight bag is filled with the mixture to prepare powders.

Formulation Example 2. Preparation of Tablets phenanthroindolizidine and phenanthroquinolizidine alkaloid derivative compounds 200 mg
corn starch 100 mg
lactose 100 mg
magnesium stearate 2 mg The above ingredients are mixed and then tableted according to a conventional preparation method of tablets to prepare tablets.

Formulation Example 3. Preparation of Capsules phenanthroindolizidine and phenanthroquinolizidine alkaloid derivative compounds 200 mg
crystalline cellulose 3 mg
lactose 14.8 mg
magnesium stearate 0.2 mg According to a conventional capsule preparation method, the above ingredients are mixed a gelatin capsule is filled with the mixture to prepare a capsule preparation.

Formulation Example 4. Preparation of Injection phenanthroindolizidine and phenanthroquinolizidine alkaloid derivative compounds 200 mg
mannitol 180 mg
sterile distilled water for injection 2,974 mg
$N_2HPO_4 \cdot 12H_2O$ 26 mg According to a conventional method for preparing injections, injections are prepared with a content of the above ingredients per one ampoule (2 mL).

Formulation Example 5. Preparation of Liquid Formulation phenanthroindolizidine and phenanthroquinolizidine alkaloid derivative compounds 200 mg
isomerase 10 g
mannitol 5 g
purified water (adequate amount)

According to a conventional method for preparing liquid preparations, each component was added to purified water to be dissolved; an appropriate amount of a lemon flavor was added thereto; the above components were mixed and then purified water was added to a final volume of 100 mL; and a brown bottle was filled with the resultant and sterilized to prepare a liquid preparation.

The foregoing descriptions of the present disclosure are provided for illustration purposes, and those of ordinary skill in the art to which the present disclosure pertains will be able to understand that the present invention can easily be modified into other specific forms without changing the technical spirit or essential features of the present disclosure. Therefore, it should be understood that the experimental examples and examples described above are illustrative in all respects and not restrictive.

INDUSTRIAL APPLICABILITY

The phenanthroindolizidine and phenanthroquinolizidine alkaloid derivative compounds of the present disclosure have excellent inhibitory effect on the activity of SARS-CoV-2 virus, which is a pathogen that causes coronavirus disease-19 (COVID-19), and thus they can be effectively used as a pharmaceutical composition for treating coronavirus disease-19.

The invention claimed is:

1. A method for treating COVID-19 (Coronavirus Disease 2019) comprising administering to a subject in need thereof a composition comprising an effective amount of a phenanthroindolizidine and phenanthroquinolizidine-alkaloid derivative compound represented by Formula 1, an optical isomer thereof, or a pharmaceutically acceptable salt thereof:

[Formula 1]

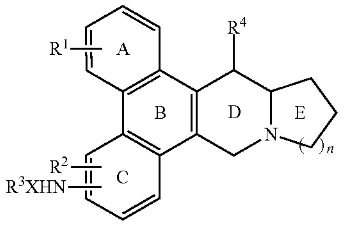

wherein, $R^1$ comprises 1 to 4 substituents independently selected from hydrogen, halogen, hydroxy, $C_1$-$C_5$ alkyl, $C_1$-$C_5$ alkoxy, carboxylic acid, amino, and $C_1$-$C_5$ alkyl amino;

$R^2$ comprises 1 to 3 substituents independently selected from hydrogen, halogen, hydroxy, $C_1$-$C_5$ alkyl, $C_1$-$C_5$ alkoxy, carboxylic acid, amino, and $C_1$-$C_5$ alkyl amino;

$R^3$ is $C_1$-$C_5$ alkyl, $C_1$-$C_5$alkoxy, or aryl;

$R^4$ is hydrogen or hydroxy;

X is CO or $SO_2$; and n is an integer of 1 or 2.

2. The method of claim 1, wherein the phenanthroindolizidine and phenanthroquinolizidine alkaloid derivative compound is one or more selected from the group consisting of the following compounds:

(R)—N-(2,3-dimethoxy-9,11,12,13,13a,14-hexahydrodibenzo-[f,h]pyrrolo[1,2-b]isoquinolin-6-yl) methanesulfonamide;

(R)—N-(2,3-dimethoxy-11,12,13,14,14a, 15-hexahydro-9H-dibenzo[f,h]pirido[1,2-b]isoquinolin-6-yl) methanesulfonamide;

methyl (2,3-dimethoxy-11,12,13,14,14a, 15-hexahydro-9H-dibenzo[f,h]pirido[1,2-b]isoquinolin-6-yl) carbamate;

N-(2,3-dimethoxy-11,12,13,14,14a,15-hexahydro-9H-dibenzo[f,h]pirido[1,2-b]isoquinolin-6-yl) propan-2-sulfonamide;

N-(2,3-dimethoxy-11,12,13,14,14a,15-hexahydro-9H-dibenzo[f,h]pirido[1,2-b]isoquinolin-6-yl)benzenesulfonamide;

N-(15-hydroxy-2,3-dimethoxy-11,12,13,14,14a, 15-hexahydro-9H-dibenzo[f,h]pirido[1,2-b]isoquinolin-6-yl) methanesulfonamide;

N-(3-chloro-2-methoxy-11,12,13,14,14a, 15-hexahydro-9H-dibenzo[f,h]pirido[1,2-b]isoquinolin-6-yl) methanesulfonamide;

N-(3-hydroxy-2-methoxy-11,12,13,14,14a, 15-hexahydro-9H-dibenzo[f,h]pirido[1,2-b]isoquinolin-6-yl) methanesulfonamide;

N-(3-ethyl-2-methoxy-11,12,13,14,14a, 15-hexahydro-9H-dibenzo[f,h]pirido[1,2-b]isoquinolin-6-yl) methanesulfonamide;

2-methoxy-6-(methylsulfonamido)-11,12,13,14,14a, 15-hexahydro-9H-dibenzo[f,h]pirido[1,2-b]isoquinolin-3-carboxylic acid;

N-(3-amino-2-methoxy-11,12,13,14,14a,15-hexahydro-9H-dibenzo[f,h]pirido[1,2-b]isoquinolin-6-yl) methanesulfonamide;

N-(2-methoxy-3-(methylamino)-11,12,13,14,14a, 15-hexahydro-9H-dibenzo[f,h]pirido[1,2-b]isoquinolin-6-yl) methanesulfonamide;

N-(2,3,7-trimethoxy-11,12,13,14,14a,15-hexahydro-9H-dibenzo[f,h]pirido[1,2-b]isoquinolin-6-yl) methanesulfonamide;

N-(6-ethyl-2,3-dimethoxy-11,12,13,14,14a, 15-hexahydro-9H-dibenzo[f,h]pirido[1,2-b]isoquinolin-5-yl) methanesulfonamide;

N-(7-chloro-2,3-dimethoxy-11,12,13,14,14a, 15-hexahydro-9H-dibenzo[f,h]pirido[1,2-b]isoquinolin-6-yl) methanesulfonamide; and N-(2,3-dimethoxy-11,12,13,14,14a,15-hexahydro-9H-dibenzo[f,h]pirido[1,2-b]isoquinolin-6-yl) acetamide.

3. The method of claim 2, wherein the phenanthroindolizidine and phenanthroquinolizidine alkaloid derivative compound is one or more selected from the group consisting of the following compounds:

(R)—N-(2,3-dimethoxy-9,11,12,13,13a,14-hexahydrodibenzo-[f,h]pyrrolo[1,2-b]isoquinolin-6-yl) methanesulfonamide;

(R)—N-(2,3-dimethoxy-11,12,13,14,14a,15-hexahydro-9H-dibenzo[f,h]pirido[1,2-b]isoquinolin-6-yl) methanesulfonamide; and methyl (2,3-dimethoxy-11,12,13,14,14a, 15-hexahydro-9H-dibenzo[f,h]pirido[1,2-b]isoquinolin-6-yl) carbamate.

4. The method of claim 1, wherein the COVID-19 is caused by severe acute respiratory syndrome coronavirus 2 (SARS-CoV-2).

* * * * *